United States Patent [19]

Kawakami et al.

[11] Patent Number: 4,902,841
[45] Date of Patent: Feb. 20, 1990

[54] METHOD FOR PRODUCING ELECTRICAL INSULATING OIL COMPOSITION

[75] Inventors: Shigenobu Kawakami, Ichikawa; Keiji Endo, Yokosuka; Hideyuki Dohi, Yokohama; Atsushi Sato, Tokyo, all of Japan

[73] Assignee: Nippon Petrochemicals Company, Ltd., Tokyo, Japan

[21] Appl. No.: 165,307

[22] Filed: Mar. 8, 1988

[30] Foreign Application Priority Data

Mar. 11, 1987 [JP] Japan ................... 62-55863
Mar. 11, 1987 [JP] Japan ................... 62-55864

[51] Int. Cl.$^4$ .................. H01B 3/22; C07C 15/12
[52] U.S. Cl. .................... 585/6.3; 585/25; 585/470; 585/471; 585/472; 585/475
[58] Field of Search .............. 585/6.3, 25, 470, 471, 585/472, 475

[56] References Cited

U.S. PATENT DOCUMENTS

| | | | |
|---|---|---|---|
| Re. 29,857 | 12/1978 | Argauer et al. | 208/111 |
| 2,282,327 | 5/1942 | Dreisback | 260/668 |
| 3,702,886 | 11/1972 | Argauer et al. | 423/328 |
| 3,714,021 | 1/1973 | Takahashi et al. | 208/232 |
| 3,753,188 | 8/1973 | Miyoshi et al. | 340/14 |
| 3,758,403 | 9/1973 | Rosinski et al. | 208/120 |
| 3,786,107 | 1/1974 | Kuribayashi et al. | 260/672 T |
| 3,790,471 | 2/1974 | Argauer et al. | 208/111 |
| 3,796,934 | 3/1974 | Munch | 317/259 |
| 3,926,782 | 12/1975 | Plank et al. | 208/135 |
| 3,965,209 | 6/1976 | Butter et al. | 260/671 |
| 4,011,274 | 3/1977 | Watanabe et al. | 260/668 |
| 4,035,285 | 7/1977 | Owen et al. | 208/120 |
| 4,111,824 | 9/1978 | Schulz et al. | 585/25 |
| 4,111,825 | 9/1978 | Schulz et al. | 252/63 |
| 4,117,026 | 9/1978 | Haag et al. | 260/671 |
| 4,228,024 | 10/1980 | Schulz et al. | 252/63 |
| 4,365,103 | 12/1982 | Chang et al. | 585/320 |
| 4,454,364 | 6/1984 | Farcasiu et al. | 585/470 |
| 4,463,209 | 7/1984 | Kursewicz et al. | 585/467 |
| 4,480,144 | 10/1984 | Smith | 585/481 |
| 4,523,044 | 6/1985 | Commandeur et al. | 585/11 |
| 4,642,730 | 2/1987 | Sato et al. | 585/6.3 |
| 4,686,548 | 8/1987 | Takashashi et al. | 503/225 |

FOREIGN PATENT DOCUMENTS

| | | |
|---|---|---|
| 226152 | 6/1987 | European Pat. Off. . |
| 3127905 | 2/1983 | Fed. Rep. of Germany ....... 585/6.3 |
| 62-55863 | 3/1987 | Japan . |
| 1463359 | 2/1977 | United Kingdom . |
| 1574523 | 9/1980 | United Kingdom . |

OTHER PUBLICATIONS

Asakura et al., "Friedel–Crafts Isomerization of Phenyltolylmethane and Ditolylmethane by Aluminum Chloride," Kinki Daigaku Kogakubu Kenkyu Hokoku 1984, 18, 49–54, (CA 105:78573v).
Chem. Abstract No. 107: 236220a, p. 740 (1987).
Chen et al., "Industrial Application of Shape Selective Catalysis" Catal. Rev.–Sci. Eng., 28 (2&3), pp. 185–264 (1986).

Primary Examiner—Robert A. Wax
Attorney, Agent, or Firm—Fisher, Christen & Sabol

[57] ABSTRACT

A method for producing an electrical insulating oil composition composed of benzyltoluene and ditolymethane. The composition is excellent in low-temperature characteristics and contains substantially no chlorine. The method comprises the steps of reacting monocyclic aromatic hydrocarbon with diarylmethane which has been prepared without using a chlorinated hydrocarbon as a starting material, at a temperature of $-10°$ to $550°$ C. in the presence of a disperoportionation catalyst to prepare a reaction product containing benzyltoluene and ditolylmethane, and recovering benzyltoluene and ditolylmethane from said reaction product by distillation.

8 Claims, No Drawings

METHOD FOR PRODUCING ELECTRICAL INSULATING OIL COMPOSITION

BACKGROUND OF THE INVENTION (1) Field of the Invention

This invention relates to a method for producing an electrical insulating oil composition which is excellent in low-temperature characteristics and which is substantially free from chlorine and chlorine-containing compound.

(2) Description of the Prior Art

West German Laid-Open Patent Publication No. 3127905 discloses that toluene is reacted with benzyl chloride in the presence of an aluminum chloride catalyst in order to prepare an electrical insulating oil composition comprising an alkylated diphenylmethane. The thus prepared electrical insulating oil has excellent low-temperature characteristics, but this method makes use of benzyl chloride as the starting material, and therefore a good deal of chlorine tends to get into the formed electrical insulating oil composition. It is considered that the electrical insulating oil containing much chlorine is poor in stability to oxidation. In addition, when the insulating oil composition lies under a high voltage, chlorine would evolve therefrom and would corrode not only elements of a container for the insulating oil but also the container itself on occasion. Further, at times, the evolved chlorine would react with the insulating oil to inconveniently produce chlorinated aromatic hydrocarbons which are generally believed to have strong toxicity.

Therefore, with regard to the insulating oils, in particular, those composed of aromatic hydrocarbons, the contamination with chlorine must be severely controlled. In short, the technique in the above-mentioned West German publication has the drawback that the insulating oil composition prepared thereby is inevitably contaminated with chlorine.

In the above-mentioned German publication, it is suggested to add thereto an acid acceptor or a stabilizer to oxidation such as a hydroquinone derivative with the intention of preventing troubles due to chlorine. Needless to say, such a measure is not a fundamental solution.

SUMMARY OF THE INVENTION

An object of this invention is to provide an electrical insulating oil composition which is substantially free from chlorine and chlorine-containing compound and which is excellent in low-temperature characteristics.

This invention is directed to a method for producing an electrical insulating oil composition composed of 20 to 80% of benzyltoluene and 80 to 20% of ditolylmethane, the aforesaid method being characterized by comprising the steps of reacting a monocyclic aromatic hydrocarbon represented by the following general formula (I) with a diarylmethane represented by the following general formula (II), which has been prepared without using a chlorinated hydrocarbon as a starting material, at a temperature of $-10°$ to $550°$ C. in the presence of a disproportionation catalyst to prepare a reaction product containing benzyltoluene and ditolylmethane, and recovering benzyltoluene and ditolylmethane from the reaction product by distillation:

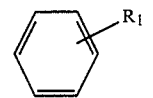

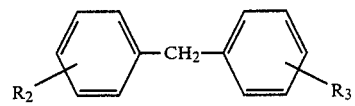

wherein each of $R_1$ to $R_3$ is a hydrogen atom or a methyl group, but when $R_1$ is the hydrogen atom, the total number of carbon atoms of $R_2$ and $R_3$ is 2, and when $R_1$ is the methyl group, the total number of carbon atoms of $R_2$ and $R_3$ is 0 or 1.

A concrete example of the monocyclic aromatic hydrocarbon of the general formula (I) is benzene or toluene, and that of the diarylmethane of the general formula (II) is diphenylmethane, benzyltoluene or ditolylmethane.

Thus, one of reactions in this invention is a reaction of disproportionating benzene and ditolylmethane, and another thereof is a reaction of disproportionating toluene and diphenylmethane or benzyltoluene.

Needless to say, in this invention, it is essential that the diarylmethane of the general formula (II), i.e., diphenylmethane, benzyltoluene and ditolylmethane all are those which have been prepared without using any chlorinated hydrocarbons.

DETAILED DESCRIPTION OF THE INVENTION

In this invention, any type of disproportionation catalyst can be used so long as it can disproportionate benzene and ditolylmethane, or toluene and diphenylmethane or ditolylmethane to form benzyltoluene and ditolylmethane.

Examples of the disproportionation catalyst include Lewis acids such as aluminum halides, e.g., aluminum chloride and aluminum bromide, a solid acid such silica-alumina, heteropoly-acids such as silicotungstic acid and phosphotungstic acid, an super-strong acid such as trifluoromethanesulfonic acid, and an inorganic strong acid type cation exchange organic resin such as perfluorosulfonic acid resin (trade name: Nafion, made by E.I. du Pont).

A temperature of the disproportionation reaction can be selected from the extensive temperature range of $-10°$ to $550°$ C., preferably $20°$ to $500°$ C., depending on a kind of disproportionation catalyst.

When the temperature of the disproportionation reaction is lower than $-10°$ C., the disproportionation reaction scarcely makes progress, and when it is higher than $550°$ C., side reactions such as decomposition and the like occur. Accordingly, both the cases are not preferable.

More particularly, the temperature of the disproportionation reaction, for example, can be selected from the range of $-10°$ to $180°$ C., preferably $20°$ to $150°$ C. when Lewis acid such as aluminum chloride is used; from the range of $180°$ to $550°$ C., preferably $200°$ to $500°$ C. in the case of an inorganic solid acid such as silica-alumina; and from the range of $140°$ to $250°$ C., preferably $150°$ to $230°$ C. in the case of a cation exchange organic resin such as perfluorosulfonic acid resin.

Ditolylmethane which is one of the raw materials of this invention is that which has been prepared without using any chlorinated hydrocarbon as the starting material. A compound prepared from the starting material which is a chlorinated hydrocarbon such as benzyl chloride, as disclosed in the above-mentioned West German patent publication, is not preferable, because the thus prepared compound often contains chlorine therein. Therefore, in this invention, for example, a compound prepared by condensing formaldehyde and toluene can be employed as the raw material. Further, this invention can accept another compound obtained by a known method without using any chlorinated hydrocarbon as the starting material. Moreover, another raw material, benzene, of this invention which will be reacted with ditolylmethane can be usually prepared from petroleum by a physical separation means such as distillation or extraction. Therefore, in general, the thus prepared benzene is substantially free from chlorine.

In addition, diphenylmethane or benzyltoluene which is one of the raw materials of this invention also is a substance which has been prepared without using any chlorinated hydrocarbon as the starting material. The above-mentioned West German publication discloses compounds prepared by using chlorinated hydrocarbons such as benzyl chloride and the like by way of the starting materials, for example, benzyltoluene prepared from toluene and benzyl chloride in the presence of an aluminum chloride catalyst, and diphenylmethane prepared by condensing benzene and chloroform under an aluminum chloride catalyst, but these compounds are not preferable to this invention, since they often contain chlorine. In consequence, it is definite that the raw material suitable for this invention is, for example, diphenylmethane prepared by condensing formaldehyde and benzene or an alkylbenzene, or benzyltoluene prepared by the disproportionation reaction of toluene and ditolylmethane in the presence of an aluminum chloride catalyst or the like. Further, this invention can accept another compound obtained by a known method without using any chlorinated hydrocarbon as the starting material. The other material, toluene, which is the partner of diphenylmethane or benzyltoluene, can be prepared from petroleum by a physical separation means such as distillation or extraction. Therefore, in general, the thus prepared toluene is substantially free from chlorine.

A molar ratio of the monocyclic aromatic hydrocarbon represented by the general formula (I) to the diarylmethane represented by the general formula (II) is suitably within the range of 0.5 to 50, preferably 1 to 30. When the molar ratio of the monocyclic aromatic hydrocarbon of the general formula (I) is less than 1, products heavier than ditolylmethane increase, and when it is more than 30, a production ratio of ditolylmethane in the product is too high, which is not economical in the manufacture of the composition of this invention where ditolylmethane should be contained in a specific ratio.

The above-mentioned reaction may be performed in a continuous system or a batch system. A reaction time is usually 20 minutes to 1 hour in the batch system and is SV 0.5 to 10 in the continuous system. A reaction pressure is not particularly limited but is usually in the range of atmospheric pressure to 10 kg/cm$^2$.

After the completion of the reaction, the catalyst is removed therefrom, if desired. Then, neutralization, washing and drying are selectively carried out to obtain a reaction product containing benzyltoluene and ditolylmethane.

Next, an electrical insulating oil comprising benzyltoluene and ditolylmethane is recovered from the reaction product by means of distillation, preferably distillation under reduced pressure. In the course of this distillation, an outflow temperature is suitably adjusted so that an amount ratio between benzyltoluene and ditolylmethane may be proper. In addition, also by separately recovering benzyltoluene and ditolylmethane from the reaction product through distillation and then mixing these compounds with each other, the insulating oil composition of this invention can be manufactured. Further, the method of this invention may be used to separately perform the reactions, thereby forming the respective reaction products. Distillation may be then carried out separately to recover benzyltoluene and ditolylmethane, followed by mixing them.

The electrical insulating oil composition produced by this invention can be used as a capacitor oil, a cable oil and the like, and it can also be suitably used as an impregnating oil for oil-impregnated electrical appliances such as oil-impregnated capacitors, oil-impregnated cables and the like in which plastics are at least partially employed as insulating materials or dielectric materials. Particularly suitable examples of the above plastics include polyesters, polyvinylidene fluoride, and polyolefins such as polypropylene, polymethylpentene and polyethylene. The suitable oil-impregnated capacitor may be prepared by winding a conductive metallic foil of aluminum or the like and a plastic film to form a capacitor element, and then impregnating the element with an insulating oil, or alternatively it may be prepared by winding, together with a selected plastic film or insulating paper, a metallized plastic film on which a conductive metallic deposition layer of aluminum or zinc is formed, in order to make a capacitor element, and then impregnating the element with an insulating oil. In like manner, the oil-impregnated cable may be prepared by winding an insulating material such as a laminated plastic composite film with a paper sheet or a plastic nonwoven fabric on a conductor such as copper, and then impregnating it with an insulating oil.

When used as an insulating oil, the electrical insulating oil of this invention may be mixed with an already known electrical insulating oil, for example, a phenylxylylethane, an alkylbiphenyl or an alkylnaphthalene in a suitably optional ratio.

Furthermore, to the electrical insulating oil of this invention, there may be added various known additives such as an antioxidant, an epoxide and a titanate series or silane series coupling agent which have been heretofore used in the insulating oils.

Benzyltoluene present in the oil composition obtained by the method of this invention contains much m-position isomer having a low melting point. Additionally, ditolylmethane in the oil composition produced by this invention also contains the position isomer in quantities in which a methyl group is bound at m-position, and therefore, the temperature to separate out crystals is low. In consequence, the electrical insulating oil composition of the present invention can inhibit the formation of crystals substantially by a mutual synergistic effect of the components, keeping up the feature of benzyltoluene that its viscosity is low at low temperatures. Further, in this invention, chlorine and chlorine-containing compounds are scarcely contained in the electrical insulating oil, and thus its stability to oxidation is good, so that the excellent non-corrosive electrical insulating oil can be manufactured.

In the present invention, benzyltoluene and ditolylmethane which are the starting materials are modified to a position isomer mixture containing a more amount of m-position isomer. The m-position isomers of benzyltoluene and ditolylmethane which are single compounds have lowest melting points in all their position isomers. For this reason, the oil composition of this invention containing the m-isomers in larger amounts can be expected to be excellent in low-temperature characteristics.

Furthermore, since the modification is made so as to produce the m-isomers in larger amounts, p-benzyltoluene, p,p'-ditolylmethane and the like, which have the highest melting points in all their position isomers and which are thus difficult to use for the electrical insulating oil, can also be employed as the starting materials.

EXAMPLE

Preparation of Oil Composition (Oil Composition 1A)

In a 10-liter separable flask were placed 3.5 liters of toluene, 1 liter of diphenylmethane and 60 g of aluminum chloride, and stirring was then carried out at 30° C. for 4 hours. After the completion of the reaction, the catalyst was inactivated, and neutralization, washing and drying were carried out, followed by distillation to recover 720 ml of an electrical insulating oil comprising benzyltoluene and ditolylmethane. The thus obtained oil was composed of 52% (by weight; the same shall apply hereinafter) of benzyltoluene and 48% of ditolylmethane. With regard to the isomer distribution of benzyltoluene, m-isomer was 63.9%, o-isomer was 10.5% and p-isomer was 25.6%. Further, ditolylmethane in which at least one methyl group was bound to the m-position was present in a proportion of 87.1%.

(Oil Composition 2A)

In a 10-liter separable flask were placed 3 liters of toluene, 1 liter of benzyltoluene and 60 g of aluminum chloride, and stirring was then carried out at 30° C. for 4 hours. After the completion of the reaction, the catalyst was inactivated, and neutralization, washing and drying were carried out, followed by distillation to recover 1200 ml of an electrical insulating oil comprising benzyltoluene and ditolylmethane. The thus obtained oil was composed of 47% of benzyltoluene and 53% of ditolylmethane. With regard to the isomer distribution of benzyltoluene, m-isomer was 59.6%, o-isomer was 10.1% and p-isomer was 23.2%. Further, ditolylmethane in which at least one methyl group was bound to the m-position was present in a proportion of 84.8%.

(Oil Composition 3A)

In a 10-liter autoclave were placed 2.8 liters of toluene, 0.7 liter of diphenylmethane and 60 g of silica-alumina, and stirring was then carried out at 260° C. for 3 hours. After the completion of the reaction, the catalyst was removed therefrom, and distillation was then carried out to recover 370 ml of an electrical insulating oil comprising benzyltoluene and ditolylmethane. The thus obtained oil was composed of 47% of benzyltoluene and 53% of ditolylmethane. With regard to the isomer distribution of benzyltoluene, m-isomer was 54.3%, o-isomer was 16.7% and p-isomer was 29.0%. Further, ditolylmethane in which at least one methyl group was bound to the m-position was present in a proportion of 80.6%.

(Oil Composition 4A)

In a 10-liter autoclave were placed 2.8 liters of toluene, 0.7 liter of diphenylmethane and 20 g of Nafion (trade name), and stirring was then carried out at 190° C. for 3 hours. After the completion of the reaction, the catalyst was removed therefrom, and distillation was then carried out to recover 480 ml of an electrical insulating oil comprising benzyltoluene and ditolylmethane. The thus obtained oil was composed of 51% of benzyltoluene and 49% of ditolylmethane. With regard to the isomer distribution of benzyltoluene, m-isomer was 59.3%, o-isomer was 13.4% and p-isomer was 27.1%. Further, ditolylmethane in which at least one methyl group was bound to the m-position was present in a proportion of 83.4%.

(Oil Compositions 5A and 6A)

The same procedure as in the preparation of the oil composition 1A was repeated to produce a mixture of benzyltoluene and ditolylmethane, and the mixture was then distilled to obtain benzyltoluene and ditolylmethane separately. These components were mixed in weight ratios of 9:1 and 1:9, respectively, in order to prepare electrical insulating oils of oil compositions 5A and 6A.

(Oil Composition 7A)

In a 2-liter separable flask were placed 730 g of toluene and 10 g of aluminum chloride, and while stirring was carried out at 70° C., 210 g of benzyl chloride was added thereto over 2 hours and the resulting mixture was further stirred for 2 hours. After the completion of the reaction, the catalyst was removed therefrom, distillation was carried out to obtain 190 g of an electrical insulating oil comprising 40% of benzyltoluene and 60% of ditolylmethane.

It is to be noted that in the oil compositions 1A to 4A, diphenylmethane used therein was that which had been obtained by condensing benzene and formaldehyde in the presence of a sulfuric acid catalyst, and benzyltoluene was that which had been obtained by disproportionating benzene and ditolylmethane in the presence of an aluminum chloride catalyst.

(Oil Composition 1B)

In a 10-liter separable flask were placed 3.3 liters of benzene, 1 liter of ditolylmethane and 60 g of aluminum chloride, and stirring was then carried out at 30° C. for 4 hours. After the completion of the reaction, the catalyst was inactivated, and neutralization, washing and drying were carried out, followed by distillation to recover 710 ml of an electrical insulating oil comprising benzyltoluene and ditolylmethane. The thus obtained oil was composed of 51% of benzyltoluene and 49% of ditolylmethane. With regard to the isomer distribution of benzyltoluene, m-isomer was 63.5%, o-isomer was 10.5% and p-isomer was 26.0%. Further, ditolylmethane in which at least one methyl group was bound to the m-position was present in a proportion of 86.9%.

(Oil Composition 2B)

In a 10-liter autoclave were placed 2.4 liters of benzene, 0.8 liter of ditolylmethane and 60 g of silica-alumina, and stirring was then carried out at 260° C. for 3 hours. After the completion of the reaction, the catalyst was removed therefrom, and distillation was then carried out to recover 380 ml of an electrical insulating oil comprising benzyltoluene and ditolylmethane. The thus obtained oil was composed of 46% of benzyltoluene and 54% of ditolylmethane. With regard to the isomer distribution of benzyltoluene, m-isomer was 53.8%, o-isomer was 16.9% and p-isomer was 29.3%. Further, ditolylmethane in which at least one methyl group was bound to the m-position was present in a proportion of 80.6%.

(Oil Composition 3B)

In a 10-liter autoclave were placed 2.4 liters of benzene, 0.87 liter of ditolylmethane and 20 g of Nafion, and stirring was then carried out at 190° C. for 3 hours. After the completion of the reaction, the catalyst was removed therefrom, and distillation was then carried out to recover 480 ml of an electrical insulating oil comprising benzyltoluene and ditolylmethane. The thus obtained oil was composed of 49% of benzyltoluene and 51% of ditolylmethane. With regard to the isomer distribution of benzyltoluene, m-isomer was 59.1%, o-isomer was 13.3% and p-isomer was 27.6%. Further, ditolylmethane in which at least one methyl group was bound to the m-position was present in a proportion of 83.0%.

(Oil Compositions 4B and 5B)

The same procedure as in the preparation of the oil composition 1B was repeated to produce a mixture of benzyltoluene and ditolylmethane, and the mixture was then distilled to obtain benzyltoluene and ditolylmethane separately. These compounds were mixed in weight ratios of 9:1 and 1:9, respectively, in order to prepare electrical insulating oils of oil compositions 4 and 5.

It is to be noted that ditolylmethane used as the raw material in the oil compositions 1B to 5B was that which had been prepared by condensing toluene and formaldehyde in a known manner.

EXAMPLE 1

(Measurement of Chlorine Content in Electrical Insulating Oil)

Amounts of chlorine in the oil compositions 1A to 7A and 1B to 5B were measured by the Wickbolt process. The amount of chlorine in the oil composition 7A was 43 ppm. In the oil compositions 1A to 6A and 1B to 5B, the amounts of chlorine were all less than 1 ppm.

EXAMPLE 2

(Investigation of Stability to Oxidation)

For the oil compositions 1A, 7A and 1B, stability to oxidation was investigated in accordance with ASTM D-1934. The results are set forth in Table 1.

TABLE 1

| Oil Composition | Test Item | |
|---|---|---|
| | Dielectric Loss Tangent (%) | Volume Resistivity (Ω) |
| Oil Composition 1A | | |
| Fresh Oil | 0.001 | $5 \times 10^{16}$ |
| Degraded without Catalyst | 0.02 | $7 \times 10^{14}$ |
| Degraded with Copper Catalyst | 0.12 | $5 \times 10^{13}$ |
| Oil Composition 7A | | |
| Fresh Oil | 0.003 | $5 \times 10^{16}$ |

TABLE 1-continued

| Oil Composition | Test Item | |
|---|---|---|
| | Dielectric Loss Tangent (%) | Volume Resistivity (Ω) |
| Degraded without Catalyst | 0.06 | $2 \times 10^{14}$ |
| Degraded with Copper Catalyst | 0.43 | $1 \times 10^{13}$ |
| Oil Composition 1B | | |
| Fresh Oil | 0.001 | $5 \times 10^{16}$ |
| Degraded without Catalyst | 0.02 | $7 \times 10^{14}$ |
| Degraded with Copper Catalyst | 0.12 | $5 \times 10^{13}$ |

The results in Table 1 indicate that the oil composition 7A containing much chlorine is poor in the stability to oxidation.

EXAMPLE 3

(Break-down Test of Capacitors)

Two biaxially oriented polypropylene films having a thickness of 14 μm were wound together with an aluminum foil which was an electrode, in order to form model capacitors having a capacity of 0.4 μF. These capacitors were impregnated with electrical insulating oils in Table 2 in an ordinary manner. They were then cooled for 1 week in a temperature cycle of −50° C. in the daytime and −60° C. in the nighttime, and afterward they were allowed to stand overnight at −50° C. and were then subjected to measurement. For the sake of the measurement, the 10 capacitors were prepared for each insulating oil composition. Potential gradient was increased every 10 V/μ at −50° C., and the number of the destroyed capacitors was counted in each potential gradient. The results are set forth in Table 2.

TABLE 2

| Oil Composition | Potential Gradient (V/μ) | | | | | | |
|---|---|---|---|---|---|---|---|
| | 40 | 50 | 60 | 70 | 80 | 90 | 100 |
| 1A | — | — | — | — | — | 1 | 9 |
| 2A | — | — | — | — | — | 2 | 8 |
| 3A | — | — | — | — | — | 2 | 8 |
| 4A | — | — | — | — | — | 1 | 9 |
| 5A | 1 | 3 | 3 | 3 | — | — | — |
| 6A | — | — | — | — | 4 | 6 | — |
| 1B | — | — | — | — | — | 1 | 9 |
| 2B | — | — | — | — | — | 2 | 8 |
| 3B | — | — | — | — | — | 1 | 9 |
| 4B | 1 | 3 | 3 | 3 | — | — | — |
| 5B | — | — | — | — | 4 | 6 | — |

As is apparent from the results in Table 2, the oil compositions 5A and 4B in which most of components is benzyltoluene have short lifetimes and show scatter of measured values.

What is claimed is:

1. A method for producing an electrical insulating oil composition consisting essentially of 20 to 80% of benzyltoluene and 80 to 20% of ditolylmethane, said method comprising the steps of reacting a monocyclic aromatic hydrocarbon represented by the following general formula (I) with a diarylmethane represented by the following general formula (II) which has been prepared without using a chlorinated hydrocarbon as a starting material, at a temperature of −10° to 550° C. in the presence of a disproportionation catalyst to prepare a reaction product containing benzyltoluene and ditolylmethane, and recovering benzyltoluene and ditolylmethane from said reaction product by distillation:

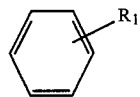 (I)

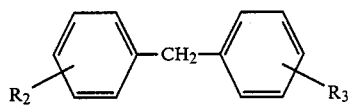 (II)

wherein each of $R_1$ to $R_3$ is a hydrogen atom or a methyl group, but when $R_1$ is the hydrogen atom, the total number of carbon atoms of $R_2$ and $R_3$ is 2, and when $R_1$ is the methyl group, the total number of carbon atoms of $R_2$ and $R_3$ is 0 or 1.

2. A method for producing an electrical insulating oil composition according to claim 1 wherein said chlorinated hydrocarbon is benzyl chloride.

3. A method for producing an electrical insulating oil composition according to claim 1 wherein said disproportionation catalyst is a Lewis acid.

4. A method for producing an electrical insulating oil composition according to claim 3 wherein said Lewis acid is an aluminum halide.

5. A method for producing an electrical insulating oil composition according to claim 1 wherein said inorganic solid acid is silica-alumina.

6. A method for producing an electrical insulating oil composition according to claim 1 wherein said strong acid type cation exchange resin is perfluorosulfonic acid resin.

7. An electrical insulating oil composition produced by the method according to claim 1.

8. A method for producing an electrical insulating oil composition according to claim 1, wherein said disproportionation catalyst is any one selected from the group consisting of an organic solid acid, a heteropoly acid, a super-strong acid and a strong type cation exchange resin.

* * * * *